(12) United States Patent
Kim et al.

(10) Patent No.: US 7,704,747 B2
(45) Date of Patent: Apr. 27, 2010

(54) DUAL BLOOD GLUCOSE METER

(75) Inventors: Moon Hwan Kim, Kyoungki-do (KR);
Keun Ki Kim, Seoul (KR); Gang Cui,
Kilimsung (CN); Hakhyun Nam, Seoul
(KR); Geun-Sig Cha, Seoul (KR)

(73) Assignee: i-SENS, Inc., Seoul (KR)

( * ) Notice: Subject to any disclaimer, the term of this patent is extended or adjusted under 35 U.S.C. 154(b) by 1272 days.

(21) Appl. No.: 10/825,253

(22) Filed: Apr. 15, 2004

(65) Prior Publication Data

US 2004/0223877 A1 Nov. 11, 2004

(30) Foreign Application Priority Data

May 7, 2003 (KR) .................. 10-2003-0028840

(51) Int. Cl.
*G01N 33/48* (2006.01)
*G01N 33/00* (2006.01)

(52) U.S. Cl. .............. 436/95; 436/94; 436/93; 436/91; 422/68.1; 422/50

(58) Field of Classification Search .......... 435/14; 600/322, 300; 205/777.5; 422/68.1; 128/633; 204/195 R, 403, 403.04, 403.01; 702/19
See application file for complete search history.

(56) References Cited

U.S. PATENT DOCUMENTS 5,366,609 A * 11/1994 White et al. .......... 204/403.04
5,661,632 A * 8/1997 Register .................. 361/679.3
6,413,213 B1 * 7/2002 Essenpreis et al. .......... 600/300
2002/0170823 A1 * 11/2002 Housefield et al. ...... 204/403.01
2003/0204313 A1 * 10/2003 Ou-Yang et al. .............. 702/19

FOREIGN PATENT DOCUMENTS

WO    WO 00/05581    * 2/2000

* cited by examiner

*Primary Examiner*—Walter D Griffin
*Assistant Examiner*—Christine T Mui
(74) *Attorney, Agent, or Firm*—Bachman & LaPointe, P.C.

(57) ABSTRACT

Disclosed herein is a dual blood glucose meter. The dual blood glucose meter includes a meter body, a measurement strip, a variety of electronic parts and upper and lower strip receiving ports. The meter body is provided with a liquid crystal display panel on the front thereof to display measured numerical values and various pieces of pictorial information. The measurement strip is brought into contact with blood at a blood collection spot so as to measure blood glucose of the blood. The electronic parts are used to measure the blood glucose of the blood. The upper and lower strip receiving ports are formed at upper and lower ends of the meter body to receive the measurement strip, and are each electrically connected to the electric parts.

4 Claims, 9 Drawing Sheets

Fig. 1

PRIOR ART

Fig. 2

PRIOR ART

Fig. 3a

PRIOR ART

Fig. 3b

PRIOR ART

DUAL BLOOD GLUCOSE METER

BACKGROUND OF THE INVENTION

1. Field of the Invention

The present invention relates generally to blood glucose meters and, more particularly, to a dual blood glucose meter, which allows a measurement strip to be inserted into one of upper and lower ends thereof, thus considerably improving the user's convenience at the time of measuring blood glucose.

2. Description of the Related Art

Recently, as the function and performance of electronic products are rapidly developing, many efforts have been made to improve the convenience of the use for electronic consumer products, such as home appliance.

Such a tendency is the same in the field of medical devices. For medical devices that consumers directly select and use, the convenience of use thereof has been stressed as much as the performance thereof has.

Of such medical devices, there is a blood glucose meter. As known well, the blood glucose meter is a device that allows diabetics, who require an adjustment of blood glucose, to easily measure the concentration of blood glucose in their blood.

In an early stage, blood glucose is measured using an early blood glucose meter installed at a hospital after a serum and corpuscles are separated from blood. Thereafter, there was developed a next generation technology that eliminated the needs of wiping away blood or removing blood corpuscles. The next generation technology is classified into a light intensity measurement method or an electrochemical measurement method. In the next generation technology, a measurement member, collectively called a strip, is used. In this case, the strip refers to only a measurement member used in the light intensity measurement method in the strict sense. The measurement member used in the electrochemical measurement method is referred to as a biosensor.

A light intensity measurement method is a method using the oxidation reaction of glucose by an oxidizing enzyme and a peroxidase as a basic principle. The light intensity measurement method is constructed so that the concentration of blood glucose is measured by analyzing a variation in the color of a reacted indicator. In the light intensity method, blood glucose is measured in such a way as to smear blood on the surface of reaction paper, to remove the blood after an elapse of predetermined reaction time, to place an opaque reflection plate under the reaction paper to reflect light, to radiate a certain amount of light from a light emitting means to the surface of the reaction paper and to utilize the amount of reflected light.

However, the light intensity measurement method is problematic in that accurate measurement is not achieved because reaction is not uniform in the case where the blood is removed when an actual reaction period exceeds or is short of an appropriate reaction period after the blood is smeared on the reaction paper. The light intensity measurement method is problematic in that the accurate measure of blood glucose because a difference in measured values occurs depending on the material of the reaction paper or force applied to the reaction paper when the blood is removed from the upper surface of the reaction paper to allow the light to be directly radiated to the reaction paper. Furthermore, the light intensity measurement method is problematic in that the use and change of the reaction paper is inconvenient and the number of the steps of measurement and measurement time are increased, thus decreasing the efficiency of measurement.

A method of measuring blood glucose proposed to overcome the above disadvantage is an electrochemical measurement method. This electrochemical measurement method is a method of measuring electrons involved in the process in which the oxidizing enzyme of glucose reacts with an electrode, using an electrical medium instead of a pigment source. When a blood sample is coated on the reacting layer of a measurement sensor used as a measurement sensor, blood glucose in the blood is oxidized by the oxidizing enzyme and the oxidizing enzyme is deoxidized. At this time, an electron acceptor oxidizes the oxidizing enzyme and deoxidizes itself. Accordingly, the deoxidized electron acceptor loses electrons and is electro-chemically oxidized again at an electron surface to which a certain voltage is applied. Since the amount of current generated at that time is proportional to the concentration of glucose in the blood, the concentration of the glucose in the blood is measured by measuring the amount of current.

As described above, a blood glucose meter for electrochemically measuring the concentration of blood glucose measures the blood glucose using the measurement of the amount of current, the concentration of blood glucose can be relatively correctly measured, measurement time can be reduced, and the performance of use, including the convenience of use, can be considerably improved.

Figure 1:
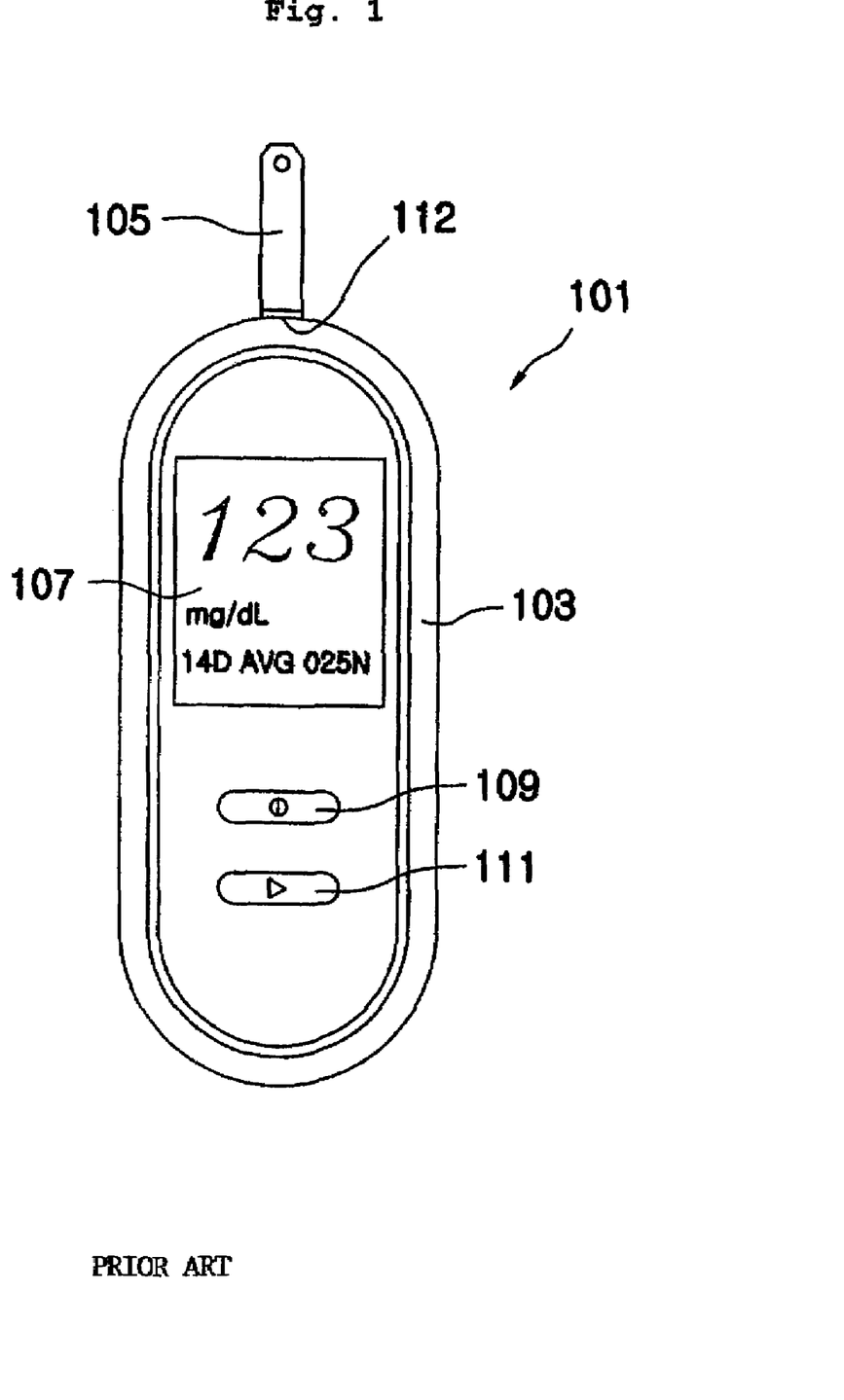
FIG. 1 is a front view of a conventional electrochemical blood glucose meter.

The electrochemical blood glucose meter is designated by reference numeral 101 in FIG. 1, and includes a meter body 103 and a measurement strip 105 inserted into an upper end of the meter body 103. As illustrated in FIG. 1, the measurement strip 105 is provided at the upper end of the meter body 103 in view of the fact that blood is collected at the tip of a finger. Furthermore, a strip receiving hole 112 is formed at the upper end of the meter body 103. A Liquid Crystal Display (LCD) panel 107 is mounted on the upper portion of the front of the meter body 103 to display a measured value and various pieces of pictorial information in the form of numbers and icons. A power switch 109 and a control switch 111 are placed in the vicinity of the panel 107.

When blood glucose is measured using the blood glucose meter 101, a drop of blood is collected in such a way as to turn on the power switch 109, clean a point of a finger from which blood is collected, remove moisture, and cut the tip of the finger using a bloodletting device. Thereafter, when the measurement strip 105 is brought into contact with the drop of blood, the value of blood glucose is displayed on the display panel 107.

Figure 2:
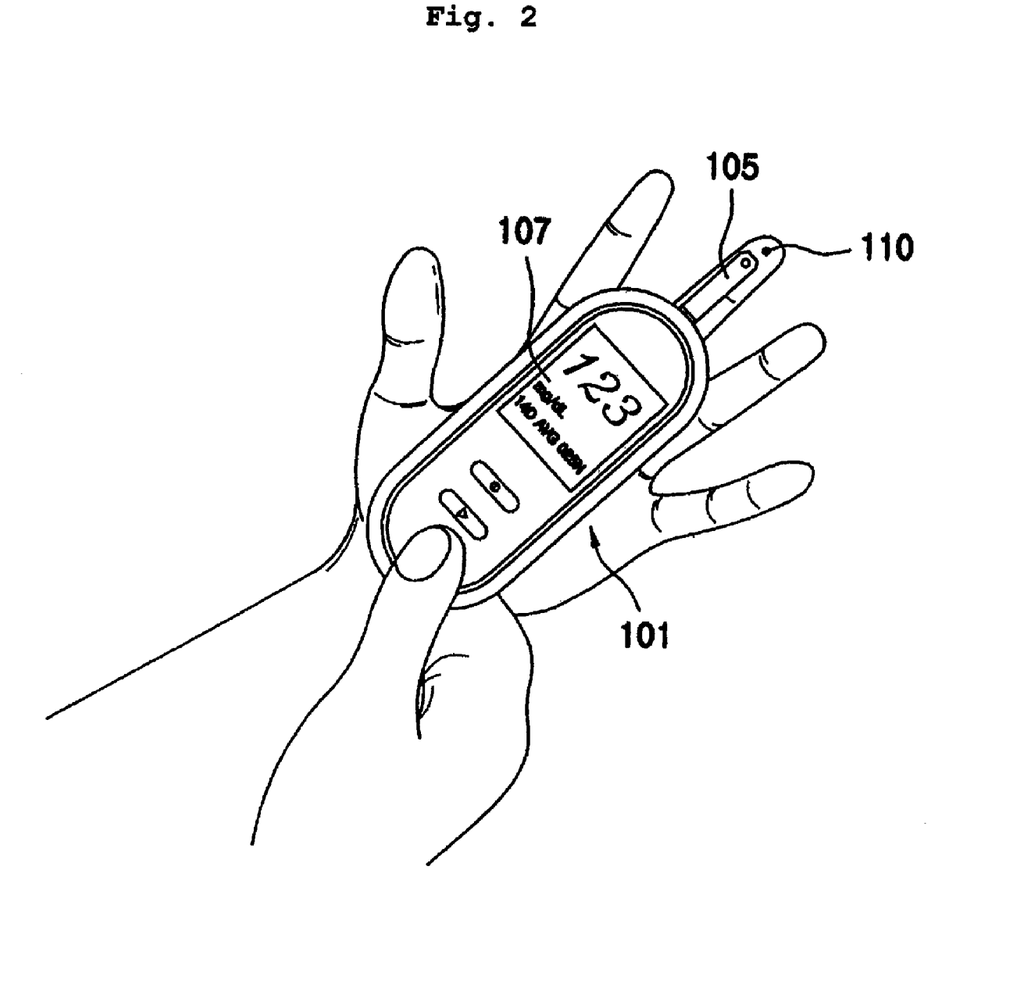
FIG. 2 is a view showing the blood glucose meter of FIG. 1 that is being used to measure blood glucose at the tip of a finger.

To measure blood glucose as described above, the tip of a finger is cut using such a bloodletting device or the like as illustrated in FIG. 2, which allows a sufficient amount of blood to be collected, but is disadvantageous in that a pain occurs at the cut point of the finger.

Figure 3A:
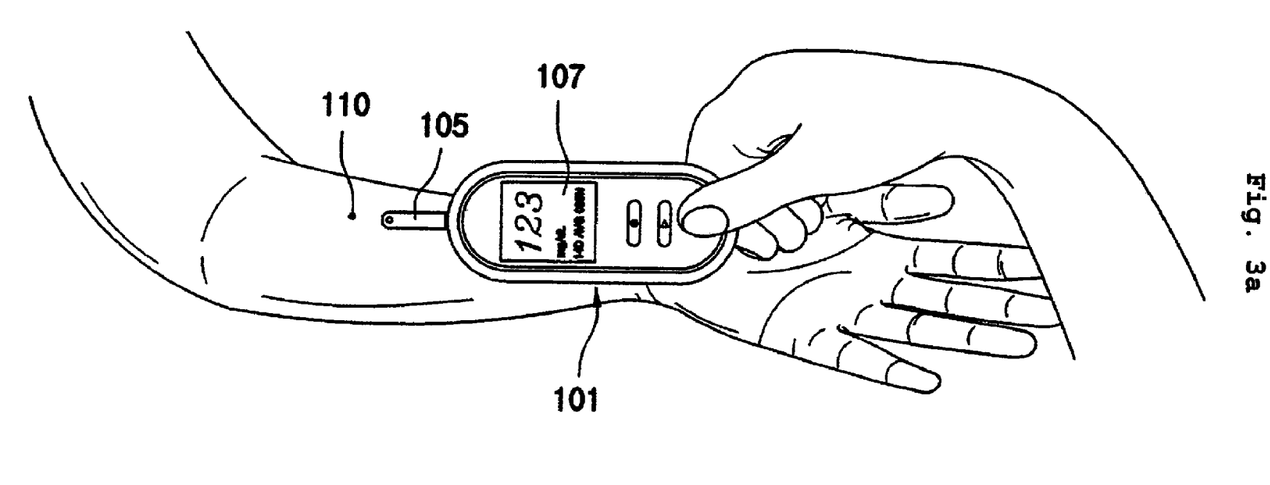
FIGS. 3a and 3b are views showing the blood glucose meter of FIG. 1 that is being used to measure blood glucose at a point of the inside of a forearm.
Figure 3B:
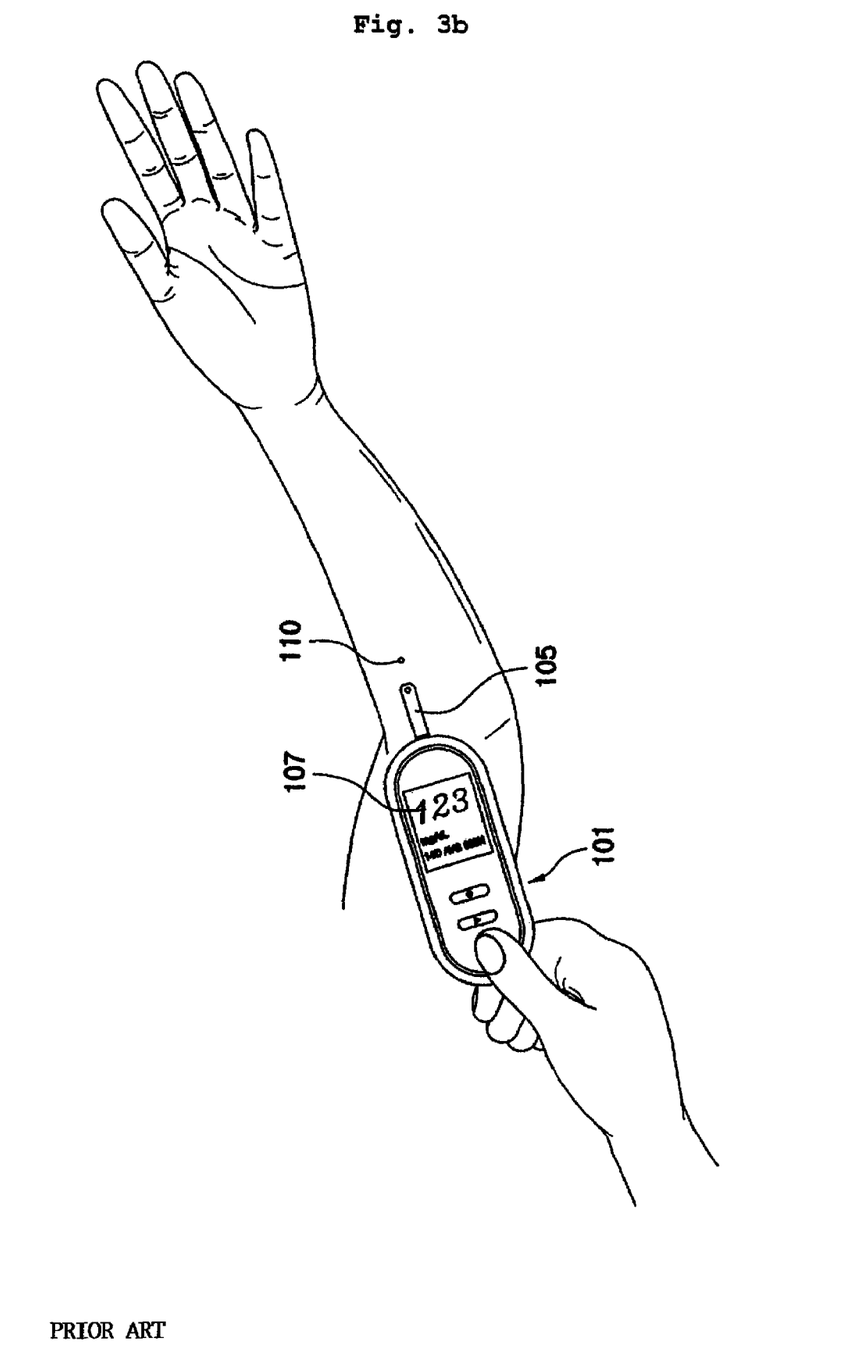

When blood is collected on at an inside point of a forearm to overcome the above-described problem, as illustrated in FIG. 3a, a pain is scarcely felt, but an inconvenience arises in that the meter body 103 is turned upside down and, thus, it becomes difficult to identify numbers or icons displayed on the display panel 107. In contrast, it is possible to bring the measurement strip 105 to a blood collection point 110 while holding the meter body 103 erect so as to allow the display panel 107 to be easily viewed, as shown in FIG. 3b. However, in this case, the right wrist gripping the blood glucose meter is excessively bent, which causes the inconvenience of use in view of ergonomics.

SUMMARY OF THE INVENTION

Accordingly, the present invention has been made keeping in mind the above problems occurring in the prior art, and an object of the present invention is to provide a dual blood glucose meter, which allows a measurement strip to be selectively inserted into upper and lower ends of the blood glucose meter, so that the measurement strip can be inserted into the upper end of the glucose meter in the same manner as in a conventional blood glucose meter, thus allowing blood to be collected at the tip of a finger, and so that the measurement strip can be inserted into the lower end of the glucose meter, thus allowing blood to be conveniently collected at a point of an arm where a pain scarcely occurs at the time of collecting blood.

In order to accomplish the above object, the present invention provides a dual blood glucose meter, comprised of a meter body provided with a display unit formed on the front thereof to display measured numerical values and various pieces of pictorial information, an upper receiving hole formed at the upper end of the above meter body for an upper measurement strip to be inserted into, and a lower receiving hole formed at the lower end of the meter body for a lower measurement strip to be inserted into.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Reference now should be made to the drawings, in which the same reference numerals are used throughout the different drawings to designate the same or similar components.

A dual blood glucose meter according to a preferred embodiment of the present invention is described in detail with reference to the accompanying drawings.

Figure 4:
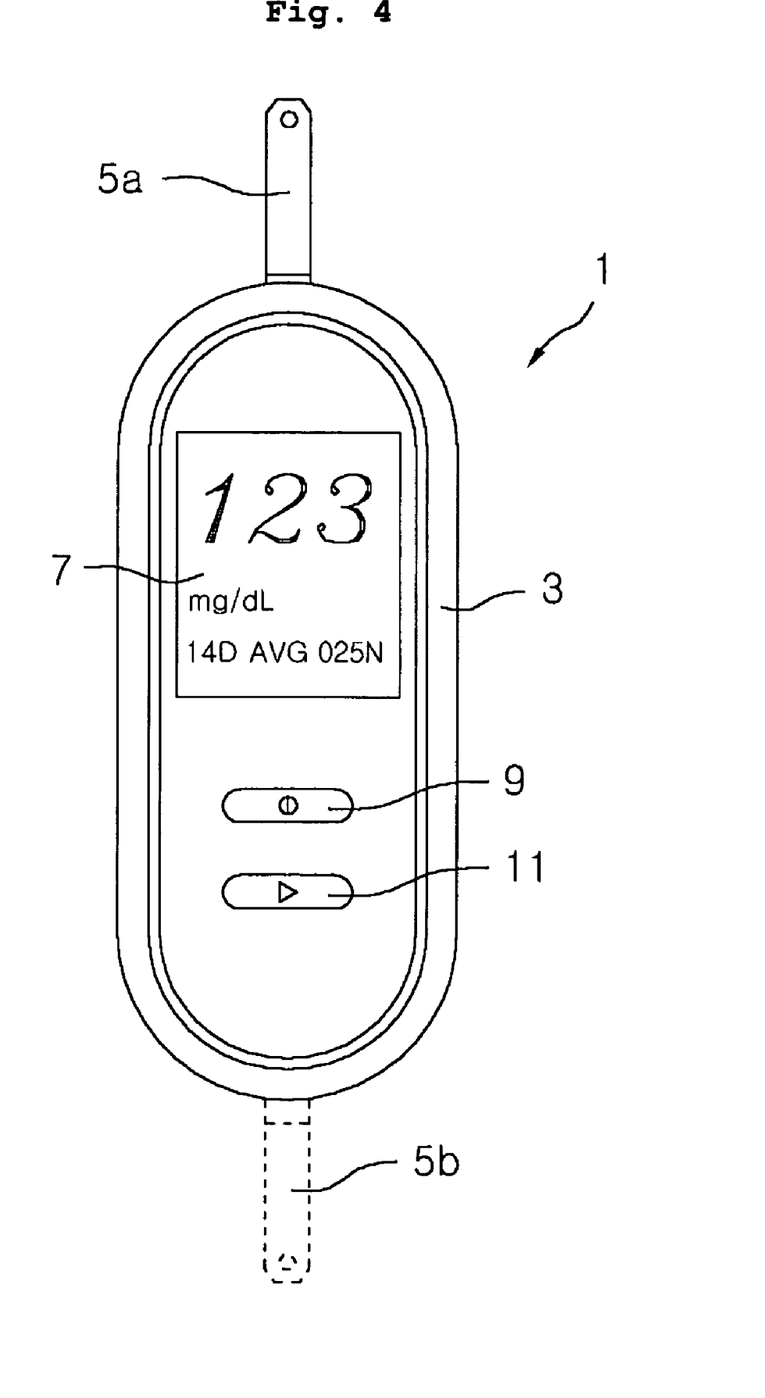
FIG. 4 is a front view of a dual blood glucose meter with a measurement strip inserted into the upper end thereof.

As shown in FIG. 4, a dual blood glucose meter(1) of the present invention comprises a meter body(3), and a display unit(7) is formed on the front of the meter body(3) to display various numerical values or various pieces of pictorial information such as notifying the sequence of blood glucose measurement or indicating measured result values. A variety of switches, including a power switch 9 for turning oh and off the dual blood glucose meter 1 and a control switch 11 for operating the blood glucose meter 1, are arranged under the upper display unit(7).

Devices such as LCD and LED etc. known in the art can be applied to the upper display unit(7), however, LCD is preferable.

Figure 5:
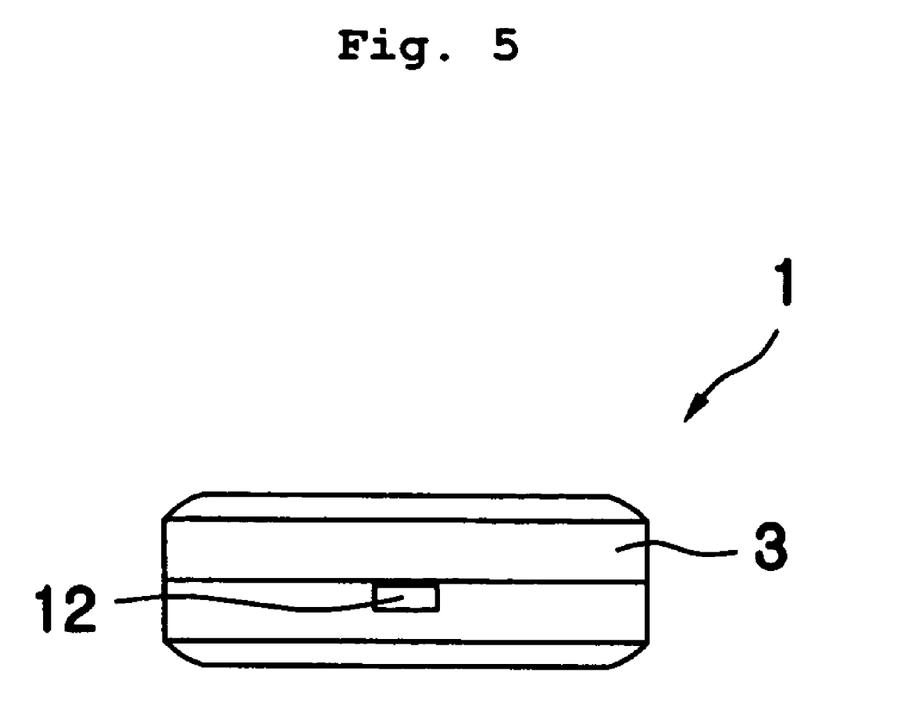
FIG. 5 is a plan view of the blood glucose meter of FIG. 4 with the measurement strip removed from the upper end thereof.

As depicted in FIGS. 4 and 5, upper and lower strip receiving holes 12 are formed inside of the upper and lower ends of the meter body (3) so as for the upper and lower measurement strips (5a, 5b) to be inserted respectively.

Figure 6:
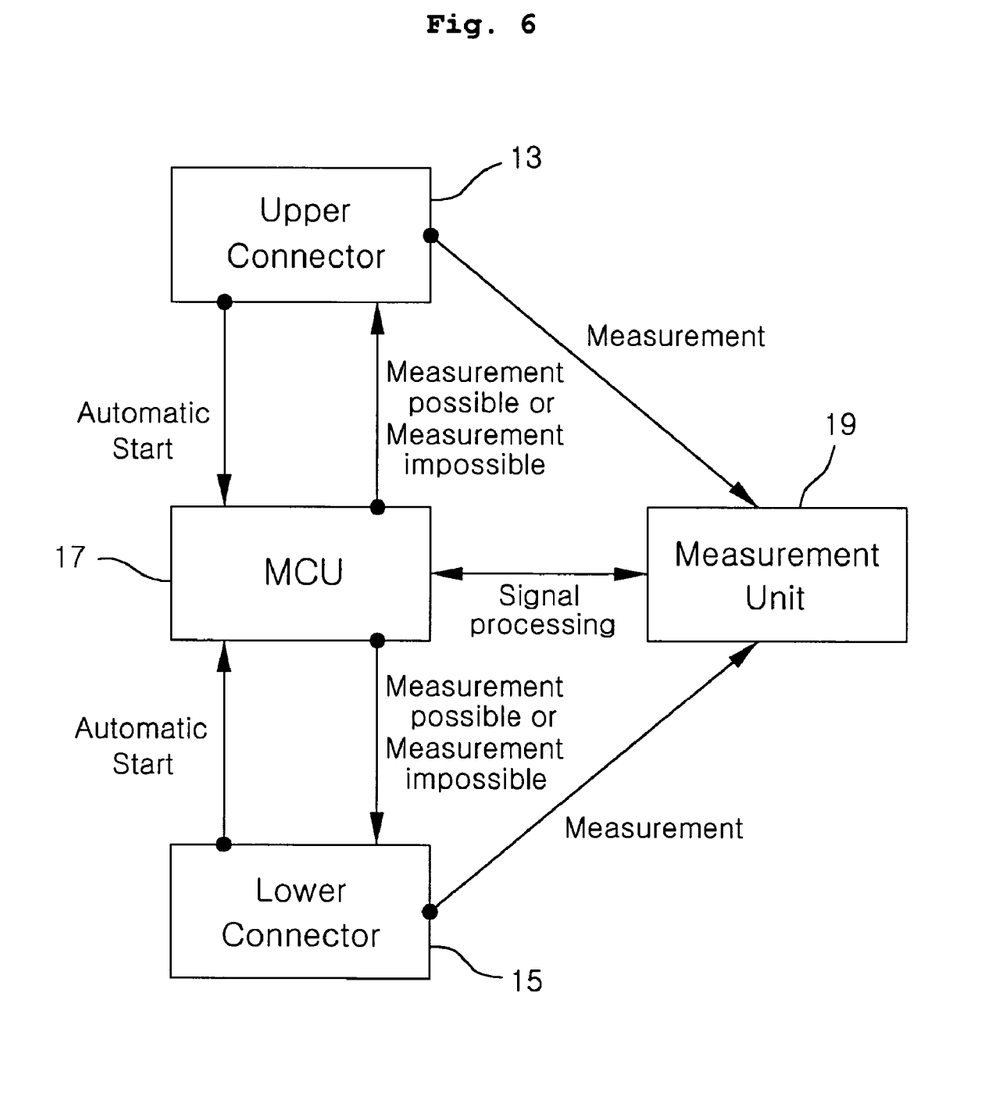
FIG. 6 is a block diagram showing the construction of the internal circuit of the blood glucose meter of FIG. 4.

Furthermore, although not shown in the accompanying drawings, a battery used as a power source is removably mounted in the rear of the meter body 3, and a circuit board electrically connected to the display unit 7, the power switch 9, the control switch 11 and the strip receiving ports 12 is placed in the inside of the meter body 3. The circuit board, as shown in FIG. 6, is provided with upper and lower connectors 13 and 15 connected to the upper and lower strip receiving holes 12, respectively, a measurement unit 19 for calculating signals generated in the connectors 13 and 15, and a Micro-Controller Unit (MCU) 17 for controlling the various parts mounted on the circuit board.

The upper and lower measurement strips(5a, 5b) to be inserted through the upper and lower receiving holes(12; shown in FIG. 5) of the upper and lower ends of the meter body(3), as shown in FIG. 4, is vertically extended to react with blood and measure blood glucose in a typical electro-chemical manner while being in contact with the blood. In particular, when blood glucose is measured at a point of a human body from which a small amount of blood flows at the time of collecting the blood, such as a point of an arm, "Bio-sensor equipped with sample introducing unit for rapidly introducing small amount of sample," which is disclosed in International Pat. Appln. No. PCT/KR2002/000703 (International Publication No. WO 03/056345) filed on Apr. 17, 2002 by the present inventor, is preferably used as the measurement strip.

When the measurement strip 5a or 5b is inserted into and connected to the upper connector 13 or lower connector 15 through the upper or lower strip receiving hole 12, the automatic start signal of the blood glucose meter 1 is transmitted to the micro-controller unit 17 so that the operation of the blood glucose meter 1 is automatically started. The micro-controller unit 17 transmits a signal indicating that measurement is possible to the upper or lower connector 13 or 15 to which the measurement strip 5a or 5b is inserted to perform the measurement, while the micro-controller unit 17 transmits a signal indicating that measurement is impossible to the upper or lower connector 13 or 15 to which the measurement strip 5a or 5b is not inserted to prevent the measurement. Accordingly, when the measurement strip 5a (or 5b) is inserted into the upper connector 13 (or lower connector 15), the upper connector (or lower connector 15) receives the signal indicating that the measurement is possible from the micro-controller unit 17 and can measure the blood glucose. In contrast, the upper connector 13 (or lower connector 15) receives the signal indicating that the measurement is impossible from the micro-controller unit 17 and cannot measure the blood glucose. Furthermore, if another measurement strip 5b (or 5a) is inserted into the lower connector 15 (or upper connector 13) when the measurement strip 5a (or 5b) has been inserted into the upper connector 13 (or lower connector 15), an error message is made to be displayed on the display panel 7.

When a blood sample is attached to the measurement strip 5a (or 5b) from a blood collection point 10 inserted into the upper connector 13 (or lower connector 15) having received the signal indicating that the measurement is possible, a measurement signal is generated, the blood glucose value of the measurement signal is calculated by the measurement unit 19, and the calculated blood glucose value is displayed on the display panel 7 through the micro-controller unit 17.

As a result, the blood glucose meter 1 of the present invention having the following operations and effects.

When blood is collected at the tip of a finger in the same manner as in a conventional blood glucose meter, blood is collected in such a way as to clean the finger where the blood is collected, to eliminate moisture from the finger and to cut the tip of the finger using a bloodletting device.

Figure 7:
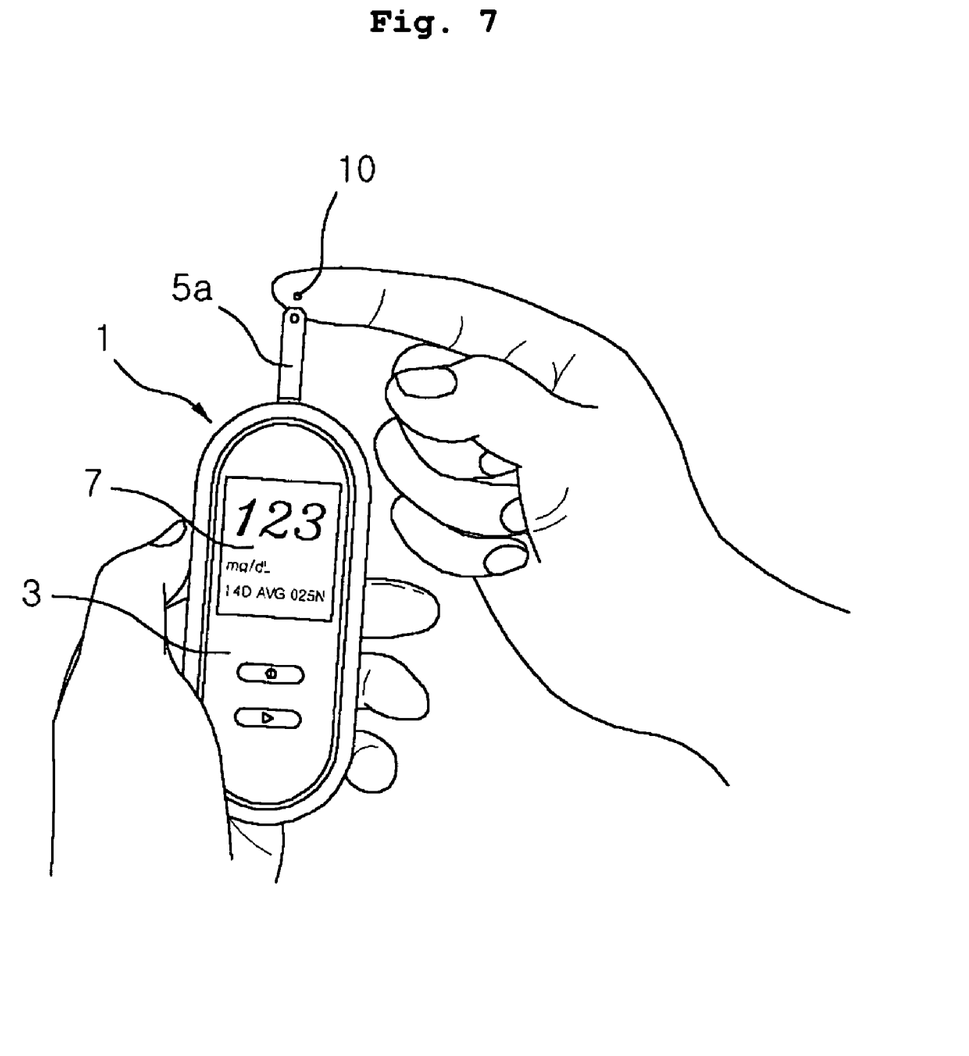
FIG. 7 is a view showing the blood glucose meter of FIG. 4 that is being used to measure blood glucose at the tip of a finger.

Thereafter, by holding the blood glucose meter 1 with the opposite hand and bringing the measurement strip 5a into contact with a blood collection point 10, as shown in FIG. 7, the measurement strip 5a is allowed to react with the blood and the value of blood glucose is made to be displayed on the display panel 7.

Figure 8:
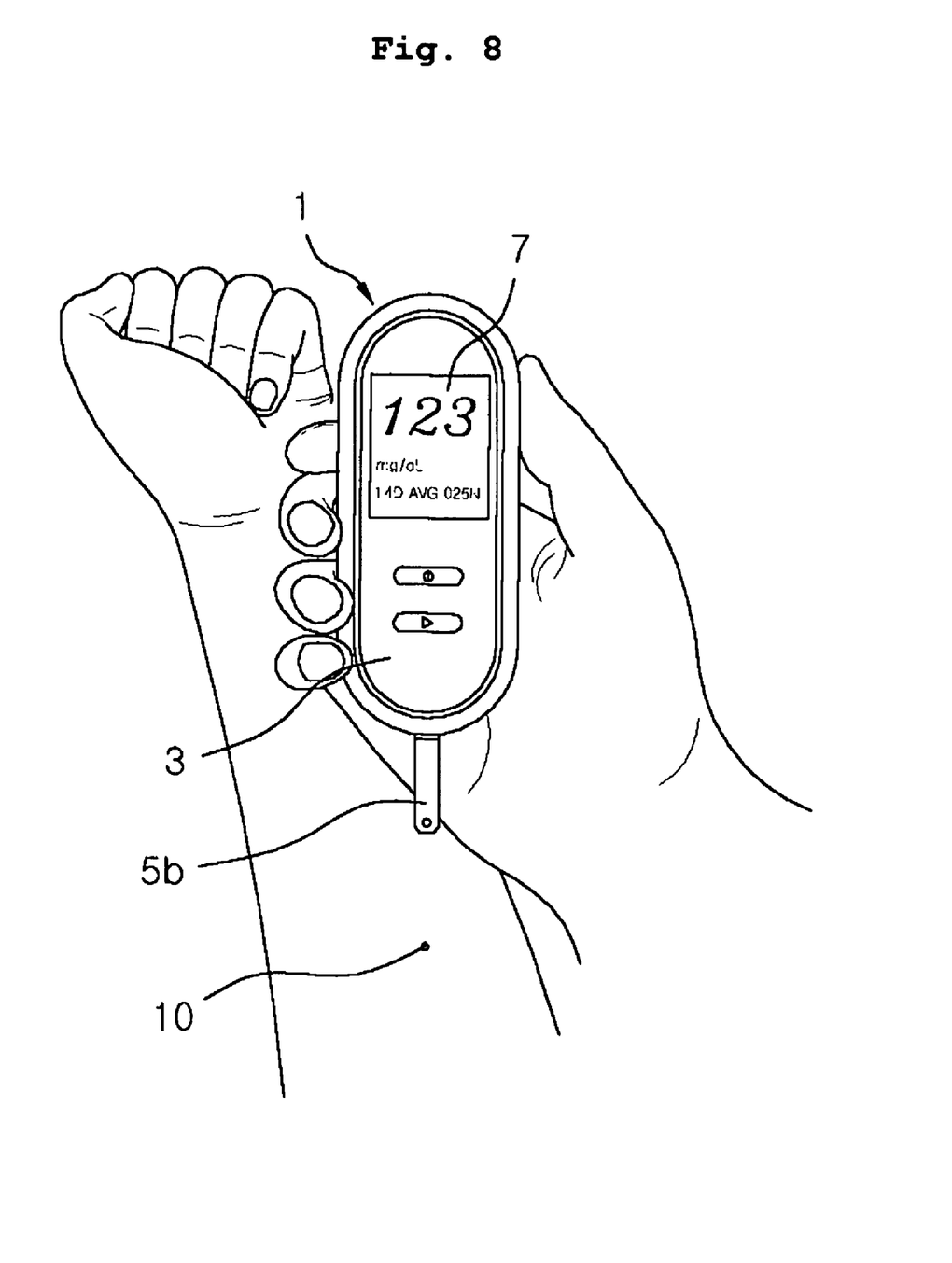
FIG. 8 is a view showing the blood glucose meter of FIG. 4 that is being used to measure blood glucose at a point of the inside of a forearm.

In contrast, when blood is collected at the blood collection point 10 of a forearm to reduce a pain at the time of collecting the blood, the measurement strip 5b is allowed to react with the blood and the value of blood glucose is made to be displayed on the display panel 7 through the medium of the value of current generated by the reaction of the measurement strip 5b with the blood, in such a way as to insert the measurement strip 5b into the lower strip receiving hole 12, to clean the blood collection point 10 of the forearm where the blood is collected, completely dry moisture at the blood collection point 10, to collect the blood using a bloodletting device, and to bright the measurement strip into contact with the blood collection point 10.

As described above, the present invention provides a dual blood glucose meter, which allows a measurement strip to be selectively inserted into upper and lower strip receiving slots. When the blood glucose meter is used with the measurement strip inserted into the upper strip receiving slot of the blood glucose meter, the blood glucose of blood can be measured at the tip of a finger of a user in a typical manner. On the other hand, when blood glucose is measured at a point of the inside of a forearm where a pain scarcely occurs at the time of collecting blood, the blood glucose can be easily measured with the measurement strip inserted into the lower strip receiving slot of the blood glucose meter without needs of turning the body of the blood glucose meter upside down and excessively bending the wrist of a hand gripping the meter body, which should be performed when blood glucose is measured with a measurement strip inserted into the upper strip receiving slot. As a result, the measurement of blood glucose can be rapidly, correctly and conveniently performed without a great pain.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A hand-held and portable dual blood glucose meter, comprising:
    a meter body (3) formed of a single display unit (7) on the front thereof to display measured numerical values and various pieces of pictorial information;
    an upper receiving hole formed on the upper end of the meter body (3) for an upper measurement strip (5a) to be inserted into;
    a lower receiving hole formed on the lower end of the meter body (3) for a lower measurement strip (5b) to be inserted into; and
    a single circuit board inside of the meter body (3), comprising:
        an upper connector (13) connected with the upper receiving hole;
        a lower connector (15) connected with the lower receiving hole;
        a single measurement unit (19) for calculating signals generated in the upper or lower connector; and
        a single micro-controller unit (17) for controlling various parts mounted on the single circuit board;
    wherein, when one measurement strip is inserted into the upper or the lower receiving hole (12) and connected to the upper or the lower connector (13 or 15), an automatic start signal of the blood glucose meter is transmitted to the micro-controller unit (17) so that the operation of the blood glucose meter is automatically started, thereafter the micro-controller unit (17) transmits a signal to one connector to which said one measurement strip is connected to perform the measurement, while the micro-controller unit (17) transmits a signal to another connector to which said one measurement strip is not connected not to perform the measurement;
    when a blood sample is attached to said one measurement strip connected to said one connector, a measurement signal is generated, the blood glucose value of the measurement signal is calculated by the measurement unit (19), and the calculated blood glucose value is displayed on the display panel (7) through the micro-controller unit (17); and
    when both the upper connector (13) and lower connector (15) are connected with the measurement strip, an error message is displayed on the display unit (7).

2. The dual blood glucose meter according to claim 1, wherein the micro-controller unit (17) transmits a measurable signal to one of the upper or lower connector (13, 15) and an un-measurable sign to the other.

3. The dual blood glucose meter according to claim 1, the display unit is LCD.

4. The dual blood glucose meter according to claim 1, wherein a display pattern of the display unit is changed according to the receiving hole into which the measurement strip is inserted.

* * * * *